(12) United States Patent
Robert et al.

(10) Patent No.: US 8,176,651 B2
(45) Date of Patent: May 15, 2012

(54) METHOD FOR DRYING OBJECTS IN A WASHER

(75) Inventors: Maxime Robert, L'Ancienne-Lorette (CA); Ghislain Parent, Saint-Isidore (CA); Louis Martineau, Saint-Nicolas (CA)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 12/885,786

(22) Filed: Sep. 20, 2010

(65) Prior Publication Data
US 2011/0005098 A1 Jan. 13, 2011

Related U.S. Application Data

(62) Division of application No. 11/934,393, filed on Nov. 2, 2007, now Pat. No. 7,841,104.

(51) Int. Cl.
*F26B 5/06* (2006.01)
*F26B 19/00* (2006.01)
*F26B 25/06* (2006.01)
*F26B 11/02* (2006.01)

(52) U.S. Cl. ........ 34/282; 34/212; 34/219; 34/225; 34/233; 34/596

(58) Field of Classification Search ............ 34/282, 34/492, 210, 219, 596, 225, 233, 212; 68/5 C, 68/20; 134/25.2, 58 D, 56 D, 57 D, 95.2
See application file for complete search history.

(56) References Cited

U.S. PATENT DOCUMENTS

| | | | | |
|---|---|---|---|---|
| 1,755,539 A | * | 4/1930 | Gerosa | 134/94.1 |
| 1,825,790 A | * | 10/1931 | Hansen | 432/199 |
| 1,827,479 A | | 10/1931 | Lierman | 422/300 |
| 1,899,005 A | * | 2/1933 | Barker | 68/183 |
| 1,939,715 A | | 12/1933 | Meitzler | 422/300 |
| 2,039,429 A | | 5/1936 | Lydon | 432/176 |
| 2,065,895 A | | 12/1936 | Jandat | 422/105 |
| 2,127,932 A | | 8/1938 | Pellkofer | 422/300 |
| 2,225,817 A | | 12/1940 | Arnold | 422/300 |
| 2,289,890 A | | 7/1942 | Walter | 134/30 |
| 2,294,904 A | | 9/1942 | Hewitt | 248/635 |
| 2,340,206 A | | 1/1944 | Richards | 422/300 |
| 2,440,043 A | * | 4/1948 | Gould | 34/87 |
| 2,591,290 A | * | 4/1952 | Rasmussen | 210/365 |

(Continued)

FOREIGN PATENT DOCUMENTS

DE 25 56 035 6/1977

(Continued)

*Primary Examiner* — Kenneth Rinehart
*Assistant Examiner* — Corey J Hall
(74) *Attorney, Agent, or Firm* — Kusner & Jaffe; Michael A. Centanni

(57) ABSTRACT

A method of drying articles within a washer comprising:
creating an airflow from an upper compartment of a chamber to a lower compartment of the chamber through a gap such that a curtain of air is formed along side walls of the chamber;
creating an air flow from the lower compartment to the upper compartment through an opening therebetween wherein a portion of the curtain of air is drawn in a first direction over articles in the lower compartment and a portion of the curtain of air continues along the side walls and is redirected in a second direction over the articles in the lower compartment;
heating the air in the upper compartment to a temperature sufficient to vaporize fluid in the chamber;
venting a portion of the air in the lower compartment; and
introducing clean filtered air into the upper compartment.

6 Claims, 5 Drawing Sheets

U.S. PATENT DOCUMENTS

| | | | | |
|---|---|---|---|---|
| 2,966,573 A | * | 12/1960 | Hansen | 219/400 |
| 3,352,627 A | * | 11/1967 | Indreland | 8/137 |
| 4,010,341 A | * | 3/1977 | Ishammar | 219/400 |
| 4,042,805 A | | 8/1977 | Kopacz | 219/492 |
| 4,098,616 A | * | 7/1978 | Dorius et al. | 134/25.2 |
| 4,395,233 A | | 7/1983 | Smith et al. | 432/176 |
| 4,698,487 A | * | 10/1987 | Meister | 219/506 |
| 4,700,685 A | * | 10/1987 | Miller | 126/20 |
| 5,185,939 A | | 2/1993 | Kimura | 34/105 |
| 5,279,799 A | | 1/1994 | Moser | 422/292 |
| 5,355,900 A | | 10/1994 | Sakata | 134/95.2 |
| 5,361,749 A | * | 11/1994 | Smith et al. | 126/21 A |
| 5,460,157 A | | 10/1995 | Prabhu | 126/21 A |
| 5,979,472 A | | 11/1999 | Lowery et al. | 134/58 R |
| 6,410,890 B1 | * | 6/2002 | Kohlstrung | 219/401 |
| 6,936,434 B2 | | 8/2005 | McDonnell et al. | 435/31 |
| 7,108,000 B2 | | 9/2006 | Lagace | 134/98.1 |
| 7,223,943 B2 | * | 5/2007 | Kohlstrung et al. | 219/400 |
| 2002/0159917 A1 | | 10/2002 | Swart et al. | 422/20 |
| 2002/0178765 A1 | | 12/2002 | Matsuda et al. | 68/20 |
| 2003/0086820 A1 | | 5/2003 | McDonnell et al. | 422/28 |
| 2003/0140517 A1 | * | 7/2003 | Schmid | 34/78 |
| 2003/0190257 A1 | | 10/2003 | Halstead et al. | 422/28 |
| 2004/0261825 A1 | | 12/2004 | Lagace | 134/95.2 |
| 2005/0223583 A1 | | 10/2005 | Lee et al. | 34/73 |
| 2006/0278257 A1 | | 12/2006 | Jerg et al. | 134/56 |

FOREIGN PATENT DOCUMENTS

JP       2007-98021       4/2007

* cited by examiner

METHOD FOR DRYING OBJECTS IN A WASHER

This application is a divisional of application Ser. No. 11/934,393 filed on Nov. 2, 2007 now U.S. Pat. No. 7,841,104.

FIELD OF THE INVENTION

The present invention relates generally to washers and more particularly to a method for drying articles in a washer. The present invention is particularly applicable to medical washers for washing medical, dental, pharmaceutical, veterinary or mortuary instruments and devices. It is contemplated that the present invention may also find application in other apparatus wherein articles are to be dried.

BACKGROUND OF THE INVENTION

Medical, dental, pharmaceutical, veterinary or mortuary instruments and devices that are exposed to blood or other body fluids require thorough cleaning and microbial deactivation between each use. Washer decontamination systems are now widely used to clean and deactivate instruments and devices. Washer decontamination systems typically operate by exposing the medical devices and/or instruments to a washing solution. After exposure to the washing solution, a rinsing solution, typically water, is sprayed over the medical devices and/or instruments to remove the washing solution. The medical devices and/or instruments are typically then dried using heated dry air.

Users of the medical devices and/or instruments typically desire that a cleaning process be as short as possible. The shorter the duration of the cleaning process, the quicker the devices can be returned to the user for use in an operation or procedure. The drying phase represents a significant portion of a cleaning process. Thus, a reduction in the duration of the drying phase will have a significant impact on the total duration of the cleaning process. The time required to dry devices in a washing chamber is influenced by many factors, including the number and placement of devices in the chamber, the amount of air flowing in the chamber, the pattern of the air flowing through chamber and the temperature of the air circulated over the devices in the chamber.

The present invention provides a washer having an improved system and method for drying articles in a washer.

SUMMARY OF THE INVENTION

In accordance with one embodiment of the present invention, there is provided a washer for washing articles. The washer is comprised of a housing defining a chamber. The housing has side walls and a top wall. A partition divides the chamber into an upper compartment and a lower compartment that is dimensioned to receive articles to be washed. The partition has an outer peripheral edge that generally conforms to the side walls of the housing. The partition is dimensioned such that a gap is formed between the edge of the partition and the side walls of the housing. An external air inlet line fluidly communicates with the upper compartment. A blower assembly is disposed in the upper compartment. The blower assembly is comprised of a housing having a first air inlet, a second air inlet and an air outlet. The first air inlet fluidly communicates with the lower compartment. The second air inlet fluidly communicates with the external air inlet line. The outlet fluidly communicates with the upper chamber. An impeller is disposed in the housing. The impeller is operable to circulate air from the lower compartment and the external air inlet line through the air outlet into the upper compartment. A heating means is disposed in the upper compartment. The heating means heats air in the upper compartment.

In accordance with another aspect of the present invention, there is provided a washer for washing articles. The washer is comprised of a housing defining a chamber. The housing has side walls and a top wall. A partition divides the chamber into an upper compartment and a lower compartment that is dimensioned to receive articles to be washed. The partition has an outer peripheral edge that generally conforms to the side walls of the housing. The partition is dimensioned such that a gap is formed between the edge of the partition and the side walls of the housing. Heating means is disposed in the upper compartment. The heating means heats air in the upper compartment. An external air inlet fluidly communicates with the upper compartment. A blower assembly is disposed in the upper compartment. The blower has an inlet and an outlet. The inlet communicates with the external air inlet and the lower compartment and the outlet communicates with the upper compartment for creating an air flow path through the washer. The air flow path is from the outlet of the blower, through the upper compartment, through the gap between the partition and the side walls, through the lower compartment to the inlet of the blower. The blower also conveys air from the external air inlet to the upper compartment, wherein less than about 10% of the air flowing through the outlet of the blower comes from the external air inlet.

In accordance with another aspect of the present invention, there is provided a method of drying articles within a washer, comprising the steps of:
 a) providing a washing chamber having a partition separating the chamber into an upper compartment and a lower compartment, the partition having an outer peripheral edge generally conforming to a shape defined by the side walls and being dimensioned to form a gap between the edge of the partition and the side walls of the chamber, the partition further including an opening centrally located in the partition, the upper compartment communicating with the lower compartment through the gap and through the opening;
 b) creating an airflow from the upper compartment to the lower compartment through the gap such that a curtain of air is formed along the side walls of the chamber;
 c) creating an air flow from the lower compartment to the upper compartment through the opening;
 d) heating the air in the upper compartment to a temperature sufficient to vaporize fluid in the chamber;
 e) venting a portion of the air in the lower compartment; and
 f) introducing clean filtered air into the upper compartment.

One advantage of the present invention is a washer for washing articles.

Another advantage of the present invention is a washer as described above having an improved cycle time.

Another advantage of the present invention is a washer wherein a cycle time is improved by reducing the drying time.

Yet another advantage of the present invention is a washer having a drying cycle that reduces the use of external air.

Another advantage of the present invention is a washer having an improved air distribution system for directing uniformly-distributed air flow over articles to be dried.

These and other advantages will become apparent from the following description of one embodiment taken together with the accompanying drawings and the appended claims.

BRIEF DESCRIPTION OF THE DRAWINGS

The invention may take physical form in certain parts and arrangement of parts, one embodiment of which will be described in detail in the specification and illustrated in the accompanying drawings which form a part hereof, and wherein.

DETAILED DESCRIPTION OF THE INVENTION

Figure 1:
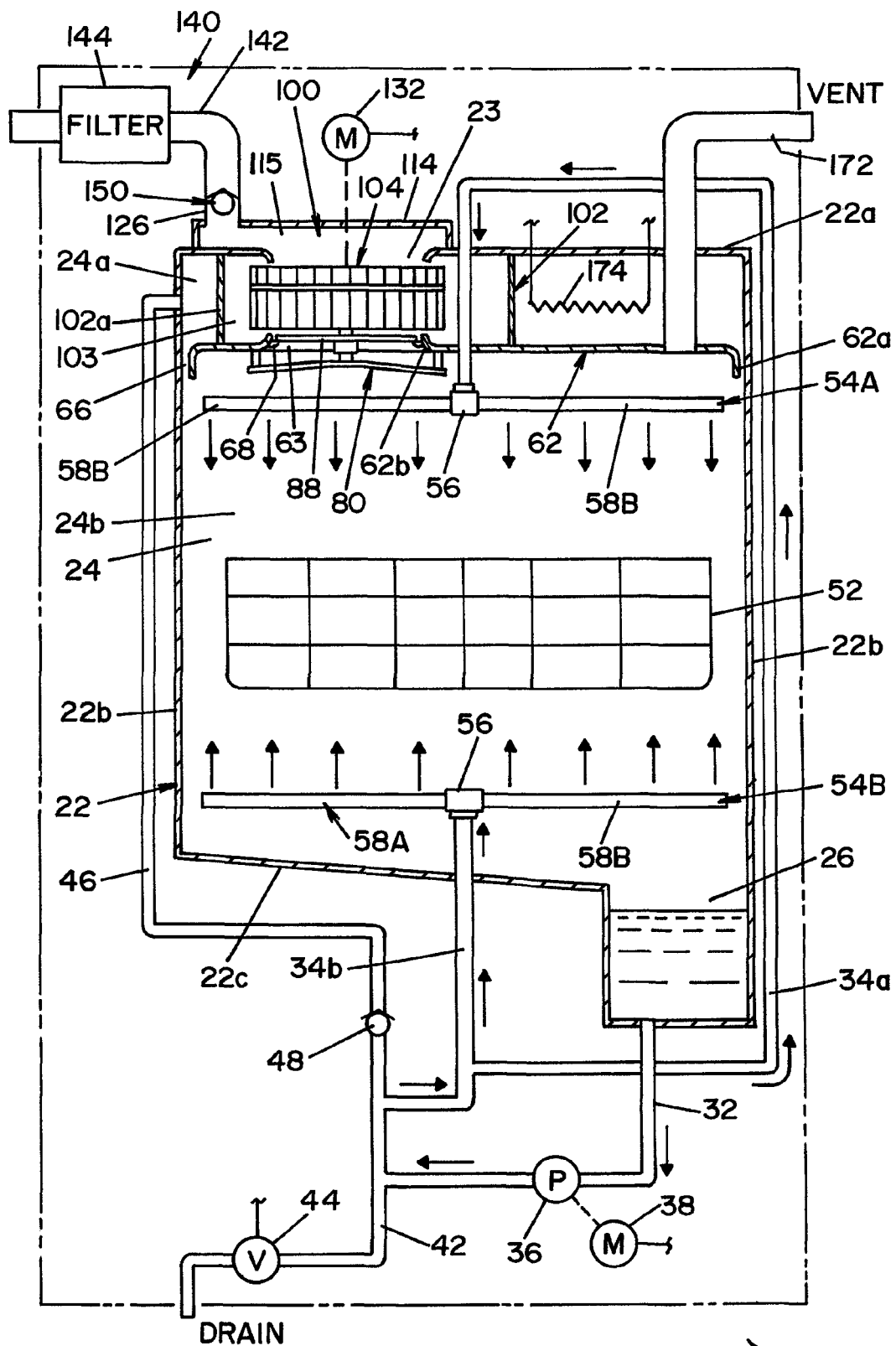
FIG. 1 is a schematic view of a washer showing one embodiment of the present invention.

Referring now to the drawings wherein the showings are for the purpose of illustrating one embodiment of the invention only, and not for the purpose of limiting same, FIG. 1 shows a schematic view of a washer 10 illustrating one embodiment of the present invention. In the embodiment shown, washer 10 is a washer for decontaminating medical instruments and/or devices. However, as will be appreciated from a reading of the specification, the present invention may find advantageous application in other types of washers and other apparatus wherein devices are to be dried.

Washer 10 is generally comprised of a housing 22 that defines a chamber 24. According to one aspect of the present invention, chamber 24 has a volume of between about 27,000 cubic inches to about 28,000 cubic inches. Housing 22 is defined by an upper wall 22a, side walls 22b and a bottom wall 22c. A circular opening 23, best seen in FIG. 1, is formed in upper wall 22a of housing 22. Opening 23 is centrally located in upper wall 22a. Bottom wall 22c is formed to include a sloped sump 26 that is disposed at the bottom of chamber 24. Sump 26 is provided to receive washing or rinsing fluids.

A circulation conduit 32 fluidly connects sump 26 to first and second branch conduits 34a, 34b having an upper and lower spray arm assembly 54A, 54B attached thereto. First branch conduit 34a extends through upper wall 22a of housing 22 and has an end disposed in an upper portion of chamber 24 with upper spray arm assembly 54A attached thereto. Second branch conduit 34b extends through bottom wall 22c of housing 22 and has an end disposed in a lower portion of chamber 24 with lower spray arm assembly 54B attached thereto. A pump 36 is provided within circulation conduit 32 for pumping fluids from sump 26 to spray arm assemblies 54A, 54B. A motor 38, schematically illustrated in FIG. 1, drives pump 36.

A drain line 42 extends from circulation conduit 32 at a location downstream from pump 36. A valve 44 is disposed in drain line 42 to control the flow of water therethrough.

A vent conduit 46 is connected to circulation conduit 32 at a location downstream of pump 36. Vent conduit 46 also communicates with the upper portion of chamber 24. A valve 48 is disposed in vent conduit 46. Valve 48 prevents the flow of fluid from circulation conduit 32 to the upper portion of chamber 24. However, valve 48 allows air to vent from the upper portion of chamber 24 to circulation conduit 32.

Washer 10 is dimensioned to contain one or more racks 52. Rack 52 is dimensioned to hold instruments and/or devices to be washed. Rack 52 is dimensioned to be disposed between upper and lower spray arm assembly 54A, 54B, as shown in FIG. 1.

Spray arm assemblies 54A, 54B are essentially identical and as such only upper spray arm assembly 54A will be described in detail. Spray arm assembly 54A is comprised of a central hub 56 with arm assemblies 58A, 58B extending therefrom, as shown in FIG. 1. Central hub 56 defines an internal cavity (not shown) that is in fluid communication with first branch conduit 34a. Central hub 56 is rotatably mounted to an end of first branch conduit 34a. Arm assembly 58A, 58B define an internal passage (not shown) that is in fluid communication with the internal cavity of central hub 56. A series of spray holes or orifices (not shown) are disposed in a wall of arm assemblies 58A, 58B at discrete locations. In the embodiment shown, spray arm assembly 54A includes two arm assemblies 58A, 58B extending therefrom. It is also contemplated that more than two, equally spaced arm assemblies may extend from central hub 56.

Figure 4:
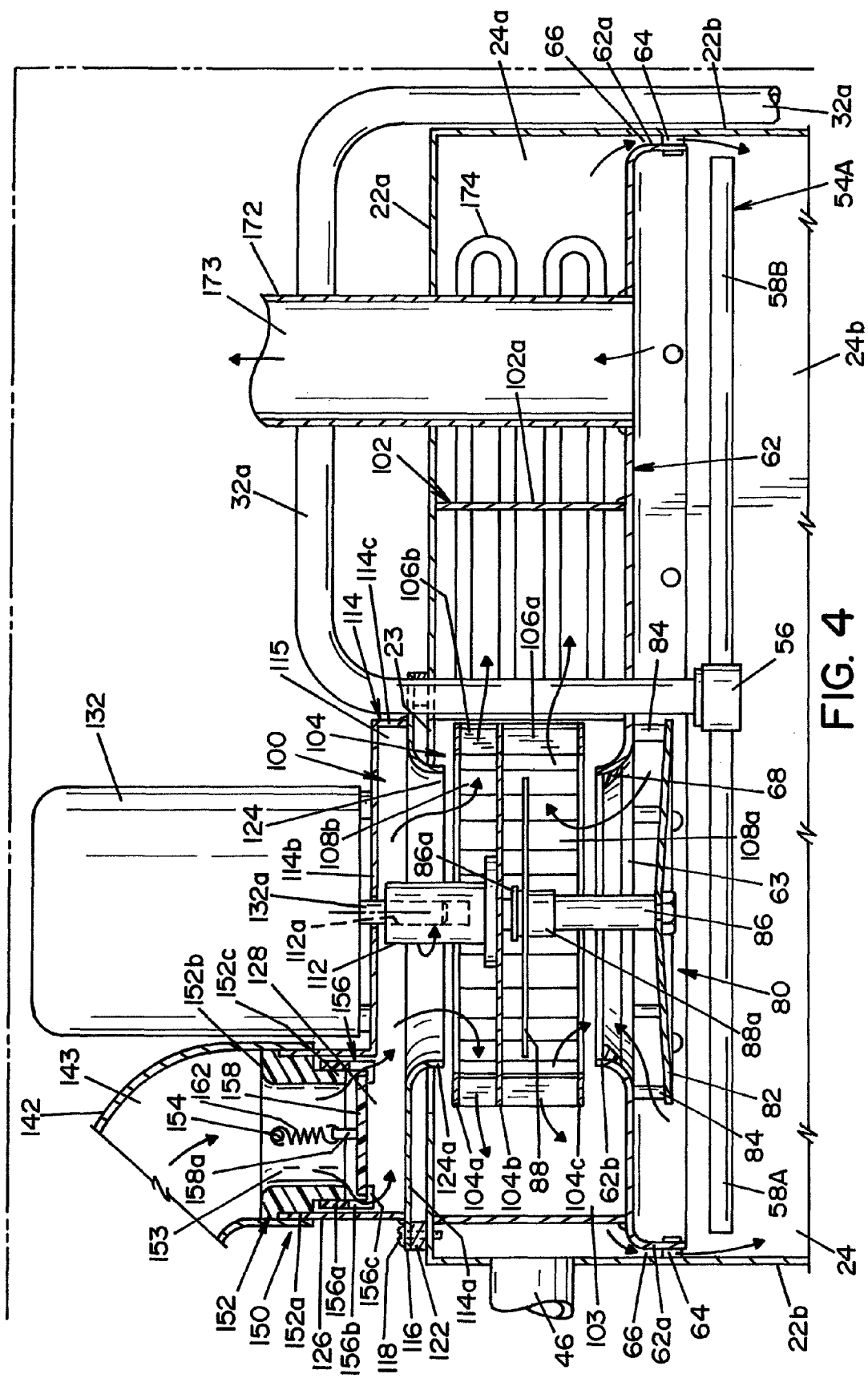
FIG. 4 is an enlarged cross-sectional view of an upper portion of the washing chamber during a drying phase.
Figure 5:
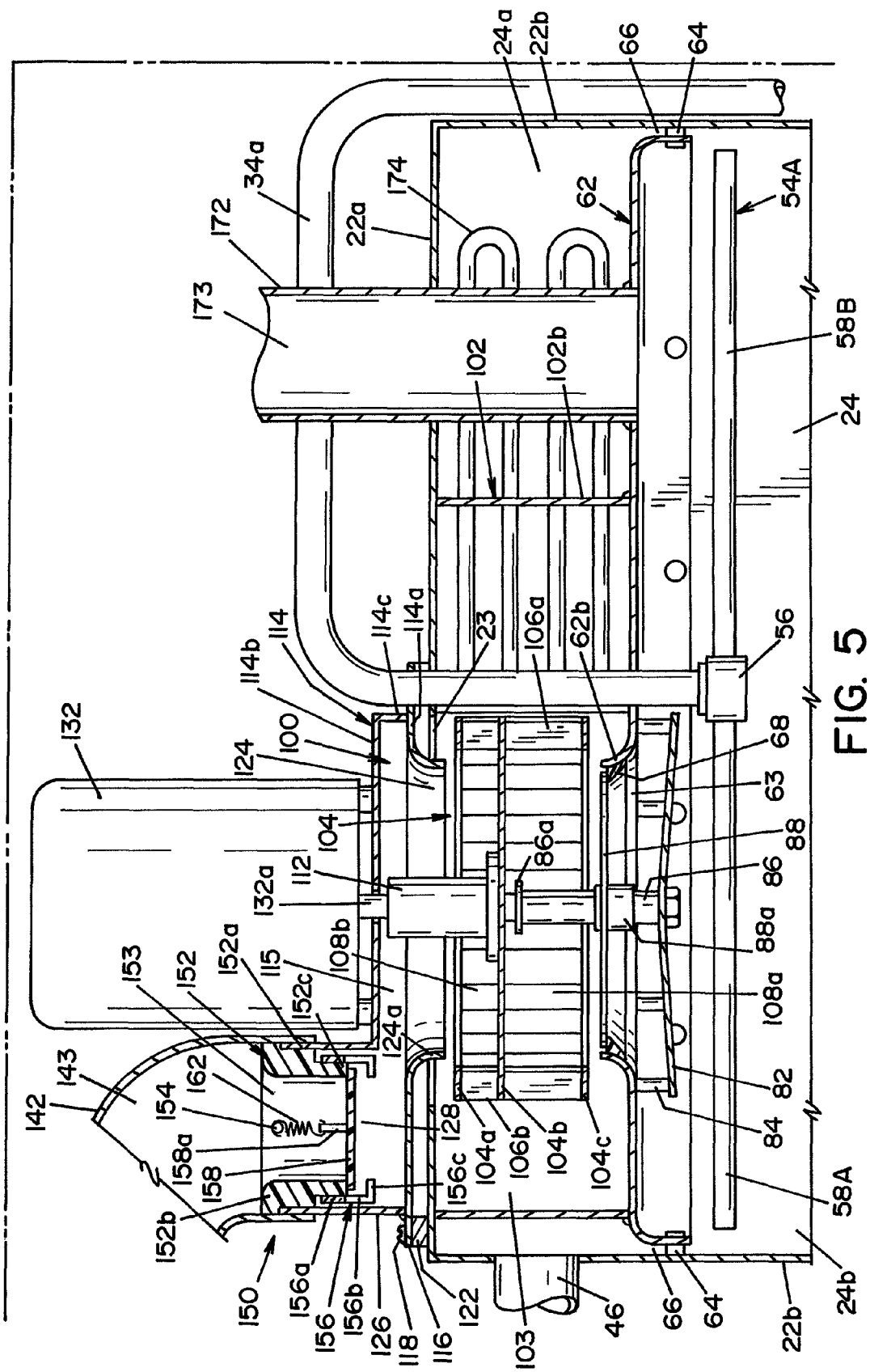
FIG. 5 is an enlarged cross-sectional view of an upper portion of the washing chamber of the present invention.

Washer 10 includes a partition 62 disposed in chamber 24. Partition 62 divides chamber 24 into an upper compartment 24a and a lower compartment 24b. Partition 62 is a generally rectangular element that has an outer peripheral edge that generally conforms to side walls 22b of housing 22. Partition 62 includes a downward facing flange 62a, best seen in FIG. 4, that extends from an outer perimeter of partition 62. In one embodiment of the present invention, partition 62 is generally cup-shaped wherein partition 62 slopes downward from a center portion to an edge of partition 62. Partition 62 is mounted to side walls 22b of washer 10 by fasteners (not shown). A plurality of spacers 64, best seen in FIGS. 4 and 5, are disposed between partition 62 and side walls 22b of housing 22. Spacers 64 are dimensioned to position partition 62 a predefined distance from side walls 22b of housing 22 such that a gap 66 is created between partition 62 and side walls 22b of housing 22.

Partition 62 also includes a circular opening 63, an upward extending flange 62b and a seal element 68, best seen in FIGS. 4 and 5. Circular opening 63 is centrally located in partition 62. Upward extending flange 62b surrounds circular opening 63. Flange 62b is formed to have a smooth radius, as best seen in FIGS. 4 and 5. Seal element 68 is disposed in opening 63. Seal element 68 is a ring-shaped element that is attached to flange 62b as best seen in FIGS. 4 and 5.

A baffle assembly 80, as best seen in FIGS. 4 and 5, is attached to partition 62 to restrict the flow of fluid through opening 63 in partition 62. Baffle assembly 80 is generally comprised of a shield 82, a post 86 and a baffle 88.

Shield 82 is disposed below opening 63 of partition 62. Shield 82 is a generally flat, disk-shaped element. Shield 82 is slightly cup-shaped such that shield 82 slopes generally downward from a center of shield 82 to an outer edge of shield 82. Shield 82 is attached to partition 62 by a plurality of fasteners (not shown). As best seen in FIGS. 4 and 5, shield 82 is spaced a predefined distance below partition 62 by a plurality of spacers 84.

Post 86 is attached to shield 82 and extends upward therefrom. Post 86 includes an outward extending flange 86a disposed at one end. In the embodiment shown, post 86 is a fastener having a head disposed below shield 82.

Baffle 88 is provided to be movably retained on post 86. Baffle 88 is generally a flat circular disk element with a sleeve 88a extending through a center thereof. Baffle 88 is dimensioned to sealingly engage seal element 68. Sleeve 88a is dimensioned to have an inner diameter to receive post 86 such that baffle 88 is moveably retained on post 86. In the embodiment shown, sleeve 88a is made of a soft polymeric material such as Teflon®. Baffle 88 is moveable along post 86 between a first position, best seen in FIG. 5, wherein baffle 88 sealingly engages seal element 68 and a second position, best seen in FIG. 4, wherein baffle 88 is disposed above seal element 68.

A blower assembly 100 is partially disposed in upper compartment 24a. Blower assembly 100 is operable to circulate air into upper compartment 24a. According to one aspect of the present invention, blower assembly 100 is dimensioned to have an output of about 1000 CFM of air. Blower assembly 100 is positioned above circular opening 63 in partition 62. Blower assembly 100 is generally comprised of a housing 102, an impeller 104, an air inlet shroud 114 and a motor 132.

Figure 3:
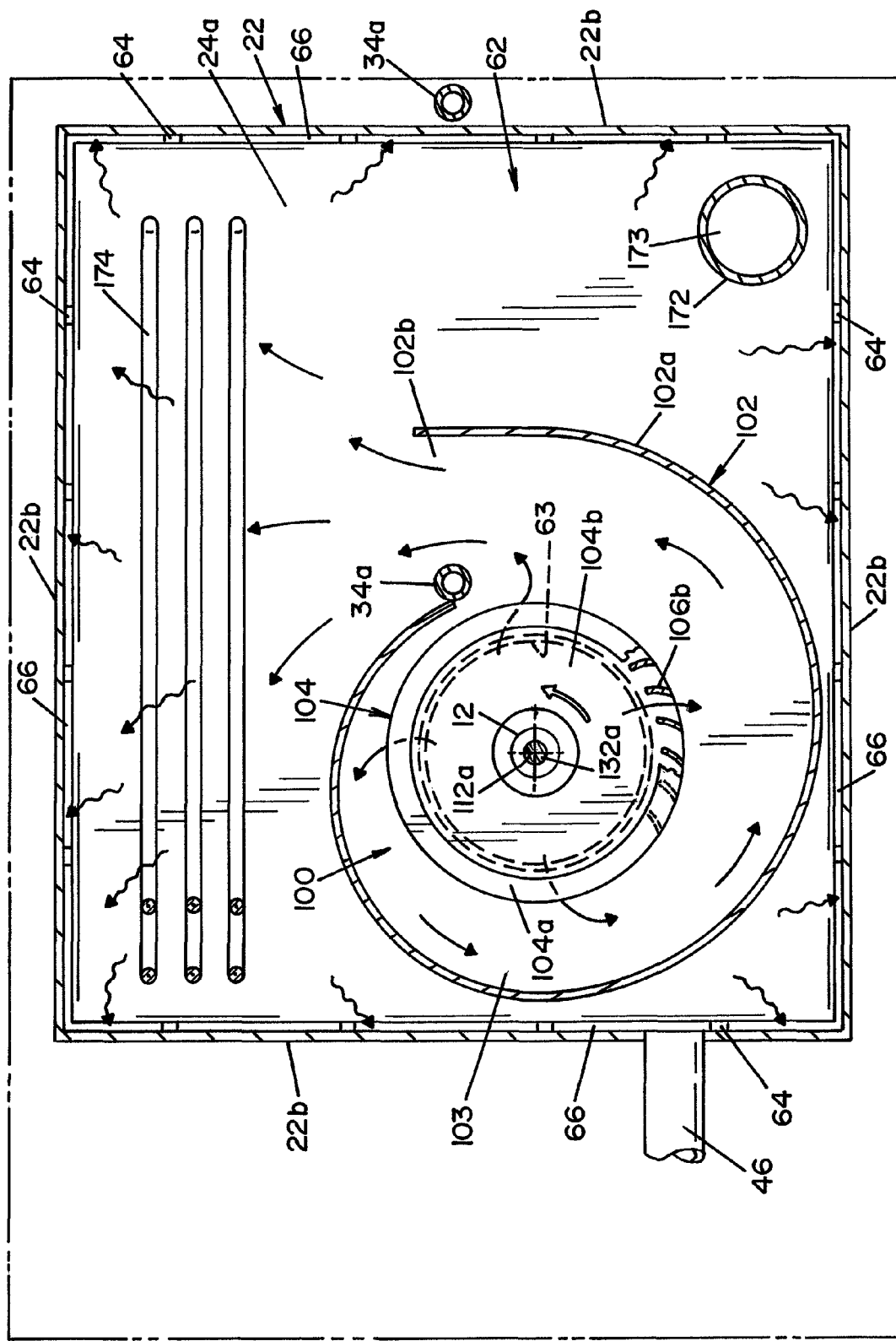
FIG. 3 is a top view, partially in section, taken along lines 3-3 of FIG. 2.

Housing 102 is defined by partition 62, upper wall 22a of housing 22 and an outer wall 102a. Housing 102 defines an inner housing cavity 103. Outer wall 102a is generally circular in shape and of an increasing radius such that outer wall 102a spirals outwardly, as best seen in FIG. 3. Outer wall 102a is formed to define an outlet 102b of housing 102, best seen in FIG. 3.

Impeller 104 is disposed in cavity 103 of housing 102. Impeller 104 is generally cylindrical in shape. Impeller 104 includes three spaced-apart circular disks, namely an upper disk 104a, a middle disk 104b and a lower disk 104c. Upper disk 104a and lower disk 104c are annular in shape and have a circular opening formed therein. Middle disk 104b is basically a flat circular plate. A series of first vanes 106a are disposed between middle disk 104b and lower disk 104c in a ring pattern as best seen in FIG. 3. A series of second vanes 106b are disposed between upper disk 104a and middle disk 104b in a ring pattern. First vanes 106a and second vanes 106b are generally curved elements, as best seen in FIG. 3. A first cavity 108a of impeller 104 is defined by first vanes 106a and middle disk 104b. A second cavity 108b of impeller 104 is defined by second vanes 106b and middle disk 104b. First cavity 108b is dimensioned to receive baffle 88, as shall be described in greater detail below. Impeller 104 includes a hub 112 that is attached to middle disk 104b. Hub 112 is generally cylindrical in shape with an axial bore 112a extending inwardly from an upper end of hub 112. As shown in FIG. 4, impeller 104 is disposed in cavity 103 of housing 102 such that impeller 104 is centrally located over opening 63 in partition 62 and centrally located under opening 23 in housing 22.

Air inlet shroud 114 is attached to upper wall 22b of housing 22. Shroud 114 defines an internal cavity 115. Shroud 114 is disposed above opening 23 in housing 22. Shroud 114 includes a bottom wall 114a, a top wall 114b and a side wall 114c. Bottom wall 114a extends beyond side wall 114c to form mounting tabs 116. A series of fasteners 118 extend through tabs 116 to mount shroud 114 to upper wall 22a. A spacer 122 is disposed between tabs 116 of shroud 114 and upper wall 22a to space shroud 114 above upper wall 22a of housing 22. Bottom wall 114a includes a circular opening 124 formed therein. Bottom wall 114a is formed to having a downward extending flange 124a that surrounds opening 124. Flange 124a is formed to have a smooth radius, as best seen in FIGS. 4 and 5. Opening 124 is centrally located over opening 23 in housing 22 such that an edge of flange 124a extends downward, away from internal cavity 115 and into opening 23 in housing 22. Top wall 114b has a circular conduit 126 that extends upward therefrom. Conduit 126 defines an internal passageway 128 that is in fluid communication with internal cavity 115 of shroud 114.

Motor 132 is attached to top wall 114b of shroud 114. Motor 132 includes a drive shaft 132a that extends downward from a lower end of motor 132. Drive shaft 132a is dimensioned to extend into bore 112a of hub 112 and attach thereto using conventionally known attachment methods. In the embodiment shown, motor 132 is a conventionally known electric motor. Motor 132, hub 112 and impeller 104 are dimensioned such that impeller 104 is disposed in cavity 103 of housing 102 and motor 132 is mounted to top wall 114b of shroud 114 using fasteners (not shown). As best seen in FIGS. 4 and 5, motor 132, impeller 104 and baffle assembly 80 are all centrally located in opening 124 of shroud 114 and opening 63 of partition 62.

An external air inlet assembly 140 is mounted to air inlet shroud 114 of blower assembly 100, best seen in FIG. 1. According to one aspect of the present invention, external air inlet assembly 140 is dimensioned to limit the flow of air therethrough relative to the output of blower assembly 100. According to one aspect of the present invention, external air inlet assembly is dimensioned to limit the flow of air therethrough to less than about 10% of the output of blower assembly 100. In the embodiment heretofore described, external air inlet assembly is dimensioned to limit the flow of air therethrough to about 50 CFM. Air inlet assembly 140 is generally comprised of an external air inlet line 142, a filter 144 and a valve assembly 150.

External air inlet line 142 is connected to conduit 126 of air inlet shroud 114. Line 142 defines an air inlet passage 143. Line 142 is attached to conduit 126 such that air inlet passage 143 is in fluid communication with passageway 128 of conduit 126 and internal cavity 115 of shroud 114.

Filter 144, schematically illustrated in the FIG. 1, is disposed in external air inlet line 142. Filter 144 is operable to filter air flowing through external air inlet line 142.

Valve assembly 150 is disposed in external air inlet line 142 to regulate flow therethrough. As best seen in FIGS. 4 and 5, valve assembly 150 is disposed at a location where external air inlet line 142 attaches to conduit 126 of shroud 114. Valve assembly 150 is generally comprised of a valve housing 152, a rod 154, a collar 156, a flat circular plate 158 and a biasing element 162.

Housing 152 is generally circular in shape with an outer surface 152a, a first end 152b and a second end 152c. Surface 152a of housing 152 is dimensioned to sealingly engage external air inlet line 142 and conduit 126, as best seen in FIGS. 4 and 5. A cylindrical valve cavity 153 extends through housing 152 from first end 152b to second end 152c. Housing 152 includes a rod 154 that is disposed near a top of valve cavity 153 and transverses valve cavity 153.

Collar 156 is attached to second end 152c. Collar 156 includes a generally tubular section 156a and a series of tabs 156b extending downward from a bottom surface of tubular section 156a. Each tab 156b has a flange 156c extending inwardly therefrom, as best seen in FIGS. 4 and 5. In one embodiment of the present invention, collar 156 is mountable to housing 152 in one of a plurality of positions, as shall be described in greater detail below.

Flat circular plate 158 is dimensioned to be received between housing 152 and collar 156, as best seen in FIG. 4. Plate 158 includes a tab 158a that extends upward from a center of plate 158. Plate 158 is movable between a first position, best seen in FIG. 5, and a second position, best seen in FIG. 4. Plate 158 sealingly engages second end 152c of housing 152 when plate 158 is in the first position. Plate 158 is disposed below second end 152c when plate 158 is in the second position.

Biasing element 162 is disposed in valve assembly 150 to bias plate 158 to the first position, i.e., towards second end 152c of housing 152. In the embodiment shown, biasing element 162 is a tension spring attached to rod 154 and tab 158a to bias plate 158 to the first position.

Figure 2:
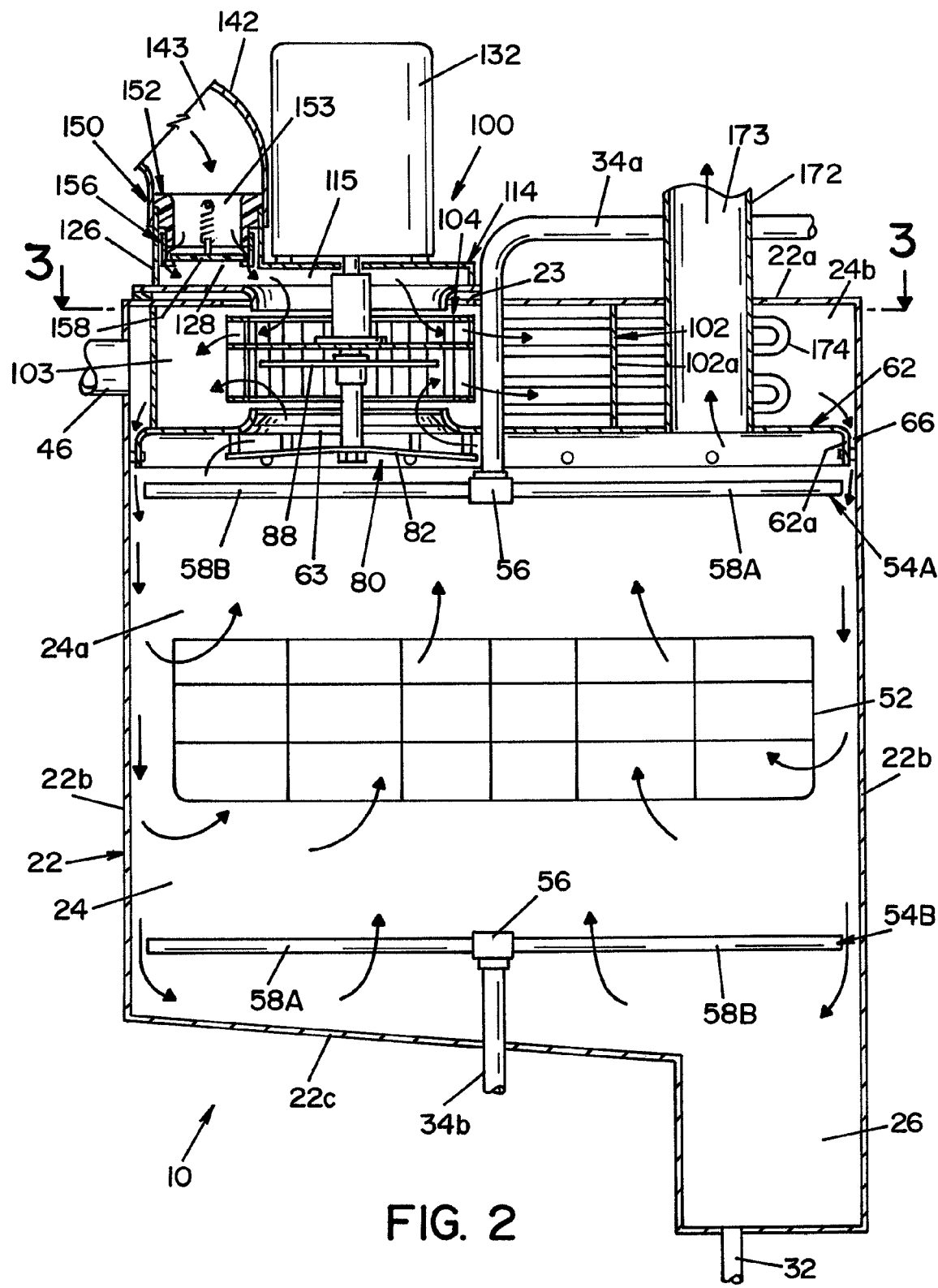
FIG. 2 is an enlarged cross-sectional view of a washing chamber of the washer shown in FIG. 1 illustrating air flow therein during a drying phase.

As best seen in FIG. 2, washer 10 includes an air vent tube 172 that extends through partition 62 and upper wall 22a of housing 22. Air vent tube 172 defines an inner passage 173. Inner passage 173 of air vent tube 172 is in fluid communication with lower compartment 24b. Another end of air vent tube 172 is connected to an exhaust or condenser (not shown). In this respect, air vent tube 172 provides fluid communication from lower compartment 24b to an exhaust or condenser.

Washer 10 also includes a heating element 174, best seen in FIG. 2, that is disposed in upper compartment 24a of chamber 24. Heating element 174 is generally an elongated member having a series of bends formed therein. According to one aspect of the present invention, heating element 174 has an output between about 8 kilowatts and about 12 kilowatts. In the embodiment disclosed herein, heating element 174 has an output of about 11.8 kilowatts. In the present embodiment, heating element 174 is an electrical resistance element connected to an electrical power source. A controller (not shown) controls heating element 174.

The invention shall further be described with relation to the operation of washer 10. One or more items to be microbially deactivated or washed, such as medical, dental, pharmaceutical, veterinary or mortuary instruments or other devices are loaded into washer 10. The items to be washed are loaded into rack 52, which in turn is placed into lower compartment 24b.

The items are microbially deactivated or washed with a microbial deactivation fluid which may be formed by exposing and mixing dry chemical reagents within chamber 24 with incoming water.

A system controller (not shown) controls the operation of washer 10 and the components therein. The operation of washer 10 includes a fill phase, an exposure phase, a rinse phase and a drying phase. Prior to an initiation of the fill phase, motor 132 is de-energized, i.e., in an "OFF" state. The weight of baffle 88 causes baffle 88 to move to the first position wherein baffle 88 sealingly engages seal element 68, as best seen in FIG. 5. In this respect, lower compartment 24b is not in fluid communication with upper compartment 24a through opening 63 in partition 62. Also, plate 158 in valve assembly 150 is biased upward by biasing element 162 to sealingly engage second end 152c of housing 152. Fluid is prevented from flowing from upper compartment 24a, through air inlet shroud 114 and into external air inlet line 142.

The system controller initiates the fill phase of washer 10. During a fill phase, water from a source (not shown) fills sump 26 with water. Once filled to a desired level, the system controller stops the flow of water to sump 26.

The system controller then initiates an exposure phase of washer 10 wherein pump 36 is energized to cause fluid to circulate along circulation conduit 32, through first and second branch conduits 34a, 34b, through upper and lower spray arm assemblies 54A, 54B and back to chamber 24, as shown by arrows in FIG. 1. In this respect, fluid flows through the cavity disposed in central hub 56, through arm assemblies 58A, 58B, and exits through spray holes (not shown). Fluid exiting the spray holes creates sprays of water that impact the devices and/or instruments disposed in rack 52. During an exposure phase, a deactivation fluid (not shown) is introduced into chamber 24. The deactivation fluid is sprayed throughout chamber 24 to deactivate the medical instruments/devices disposed therein.

Following an exposure phase, the system controller initiates a drain phase of washer 10. During the drain phase, the system controller causes valve 44 to move to an open position and motor 38 remains energized. In this respect, fluid flows from pump 36 out through drain line 42. Once the deactivation fluid is drained from sump 26, the system controller initiates a rinse phase of washer decontamination system 10.

A rinse phase of washer decontamination system 10 essentially consists of a fill phase followed by a circulation phase and a drain phase. During the rinse phase, rinse water is circulated throughout washer 10 to remove residual deactivation fluid from washer 10 and the medical devices and/or instruments in chamber 24. Successive rinse phases are performed until a concentration of deactivation fluid on the medical devices and/or instruments is below a desired level.

Following the rinse phase, the system controller initiates a drying phase of washer 10. During the fill, exposure and rinse phases, baffle 88 rests on seal element 68 to create a seal therebetween, as best seen in FIG. 5. In this position, water spray from lower chamber 24b is prevented from entering upper chamber 24a through opening 63 in partition 62 during the fill, exposure and rinse phases. Also, plate 158 in valve assembly 150 is biased upward by biasing element 162 to cause plate 158 to sealingly engage second end 152c. In this position, fluid is prevented from entering external air inlet line 142 through valve assembly 150.

During a drying phase, the system controller energizes motor 132 to turn impeller 104 of blower assembly 100. Blower assembly 100 circulates air within washer 10. Rotation of impeller 104 causes first vanes 106a to draw air from first cavity 108a of impeller 104. In this respect, an air pressure in first cavity 108a is lower than an air pressure upstream of baffle 88. The difference in air pressure between first cavity 108a and an upstream side of baffle 88 causes baffle 88 to move to the second position, as best seen in FIG. 4, wherein air flows through circular opening 63 in partition 62. Baffle 88 may move upward until bushing 88a contacts flange 86a of post 86.

Impeller 104 forces air through outlet 102b into upper compartment 24a, thereby increasing a pressure of the air in upper compartment 24a. The increase in pressure in upper compartment 24a creates air flow from upper compartment 24a to lower compartment 24a through gap 66 formed between partition 62 and side walls 22b of housing 22. A predetermined air flow pattern is created in lower compartment 24b by air flowing from upper compartment 24a into lower compartment 24b through gap 66. As seen in FIG. 2, air flows along side walls 22b and is redirected by bottom wall 22c of housing 22 upward in chamber 24. The air flows upward through racks 52 and upward over items in rack 52. A portion of the air flowing along side walls 22b is drawn towards the center of chamber 24, as shown by arrows in FIG. 2, by blower assembly 100. The air flows laterally across items in rack 52. Air in lower compartment 24b is then drawn towards opening 63 in partition 62, i.e., the inlet of blower assembly 100, as a result of the operation thereof. A first fluid flow path is formed from lower compartment 24b, through opening 63, through impeller 104 into cavity 103 of housing 102, as best seen in FIGS. 2 and 4. In this respect, opening 63 in partition 62 defines a first inlet of blower assembly 100.

The foregoing operation of blower 10 establishes a predetermined flow pattern wherein air flows from upper compartment 24a, through gap 66, through lower compartment 24b, through opening 63 to blower assembly 100. Blower assembly 100 and gap 66 are dimensioned such that a uniform curtain of air is formed along side walls 22b of housing 22 in lower compartment 24b. This flow of air downward along side walls 22*b* of housing 22 facilitates the removal of moisture that may be disposed along side walls 22*b* of housing 22. Air is directed to the corners of housing 22, which facilitates the drying of side walls 22*b* of housing 22 and items in rack 52 that may be disposed near the corners of housing 22. The flow of air upward and laterally across the items in rack 52 further facilitates the drying of the items.

During the operation of blower assembly 100, as air is circulated within washer 10, air is also drawn into washer 10 through external air inlet line 142. As stated above, the system controller energizes motor 132 to turn impeller 104 of blower assembly 100. As impeller 104 turns, second vanes 106*b* draw air from internal cavity 115 of air inlet shroud 114. In this respect, air pressure in internal cavity 115 is lower than air pressure upstream of valve assembly 150. The difference in air pressure between internal cavity 115 and the air upstream of valve assembly 150 causes plate 158 to move to the second position wherein air flows through valve assembly 150. Plate 158 moves downward. Plate 158 may move downward until plate 158 contacts flanges 156*c* of collar 156. Air is drawn through filter 144, through external air inlet line 142, through valve cavity 153 of housing 152, through internal cavity 115 of shroud 114, through impeller 104 and into cavity 103 of housing 102. As the air passes through filter 144, filter 144 filters the air flowing therethrough, thereby providing clean filtered air into washer 10. A second fluid flow path, is formed along external air inlet line 142, through filter 144, through valve cavity 153 of housing 152, through internal cavity 115 of shroud 114, through impeller 104 into cavity 103 of housing 102, as best seen in FIGS. 2 and 4. In this respect, conduit 126 in shroud 114 defines a second inlet to blower assembly 100.

The amount of air drawn through the second fluid flow path is limited by valve assembly 150. According to one aspect of the present invention, washer 10 is designed such that less than about 10% of the output of blower assembly 100 is comprised of air from the second fluid flow path, i.e., external air inlet line 142. In one embodiment of the present invention, washer 10 is designed such that less than about 5% of the output of blower assembly 100 is comprised of air from the second fluid flow path, i.e., external air inlet line 142. In the embodiment described above, blower assembly 100 is dimensioned to have an output of about 1000 CFM and external air inlet assembly 140 limits the air flowing along the second fluid flow path to about 50 CFM. In this embodiment, about 5% of the output of blower assembly 100 is comprised of air from the second fluid flow path. In accordance with one aspect of the present invention, collar 156 may be adjusted upward and downward relative to housing 152. In this respect, collar 156 may be adjusted to control the amount of air flowing through valve assembly 150.

During the operation of blower assembly 100, as air is circulated within washer 10, air drawn through external air inlet line 142 is offset by air conveyed out of lower compartment 24*b* through air vent tube 172. A portion of the air in lower compartment 24*b* flows outward through air vent tube 172 to the exhaust or a condenser (not shown). A vent air path is formed from lower compartment 24*b* through air vent tube 172 to the exhaust or condenser. An equilibrium is achieved in washer 10 wherein air entering washer 10 through the second fluid flow path is offset by air exiting washer 10 through the vent air path.

As heretofore described, the operation of blower assembly 100 causes air to circulate within washer 10 in a distinct flow pattern. Blower assembly 100 also causes air to be drawn into upper compartment 24*a* along second fluid flow path and to be released from lower compartment 24*b* along the vent air path. During the operation of blower assembly 100, heating element 174 is energized to heat the air as it flows through upper compartment 24*a*. Heating element 174 heats the air in upper compartment 24*a* further increasing the air pressure in upper compartment 24*a*. The heated air is circulated from upper compartment 24*a* to lower compartment 24*a*. In this respect, the heated air is directed along the flow pattern described above, i.e., downward along side walls 22*b* of housing 22 and upward and laterally across items in racks 52. As blower assembly 100 continuously circulates air in washer 10, heating element 174 continuously heats the air circulating in washer 10 until a predetermined temperature is achieved. According to one aspect of the present invention, heating element 174 causes the air to achieve a temperature sufficient to vaporize, i.e., evaporate, the rinse fluid on the items in racks 52 in lower compartment 24*b*. The system controller controls heating element 174 to prevent the temperature of the circulated air from exceeding a predetermined upper limit. The system controller may control heating element 174 by energizing and de-energizing heating element 174 or using other conventionally known control methods for controlling the operation of a heating element.

As stated above, in one embodiment partition 62 is generally cup-shaped such that an edge of partition 62 is lower than a center of partition 62. In this respect, fluid that collects on an upper surface of partition 62 may drip toward an edge of partition 62 and into lower compartment 24*b*. The present invention thereby provides a sloped partition 62 whereby moisture that may navigate to upper compartment 24*a* during washing and rinsing cycles does not pool therein but drips towards the edge of partition 62 and into lower compartment 24*b* where the water is vaporized during a drying cycle.

As stated above, valve 48 prevents the flow of fluid from circulation conduit 32 to upper compartment 24*a*. However, valve 48 does not prevent the flow of air in the reverse direction, from upper compartment 24*a* to circulation conduit 32. During the drying phase, a portion of the air in upper compartment 24*a* flows through vent conduit 46, past valve 48 into circulation conduit 32. The air then flows to first and second branch conduits 34*a*, 34*b*, through central hub 56 into arm assemblies 58A, 58B and out through the spray holes disposed therein. In this respect, the heated air from upper compartment 24*a* flows through circulation conduit 32, through first and second branch conduit 34*a*, 34*b*, through upper and lower spray arm assemblies 54A, 54B and into lower compartment 24*b*, to remove residual moisture therein.

The foregoing apparatus facilitates the rapid drying of articles by circulating air in a unique flow pattern in washer 10. The air is circulated between upper compartment 24*a*, wherein the air is heated, and lower compartment 24*b*. The air flows upward and laterally across the articles in rack 52 in lower compartment 24*b*. The air in washer 10 is heated to a sufficient temperature to vaporize the rinse solution on the articles in lower compartment 24*b*. In this respect, heated air flows in a unique flow pattern over articles in rack 52 to facilitate the rapid drying of the articles. As the rinse solution in lower compartment 24*b* evaporates, moist air is released from lower compartment 24*b* along the vent air path while dry, filtered air is introduced into upper compartment 24*a* along the second fluid flow path. The re-circulation of heated air in washer 10, combined with the removal of moist air from lower compartment 24*b* and the addition of dry, filtered air into upper compartment 24*a*, allows the articles in washer 10 to be dried rapidly and efficiently. The present invention thereby provides an efficient method and apparatus for drying a washer and medical devices and/or instruments disposed in a washer after exposure to a rinse solution.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A method of drying an interior of a washer and objects therein, comprising the steps of:
   a) providing a washing chamber having a partition separating said chamber into an upper compartment and a lower compartment, said partition having an outer peripheral edge generally conforming to a shape defined by side walls of said chamber and being dimensioned to form a gap between said edge of said partition and said side walls of said chamber, said partition further including an opening centrally located in said partition, said upper compartment communicating with said lower compartment through said gap and through said opening, said washer including at least one spray arm assembly disposed in said lower compartment, a vent conduit fluidly connected at one end to said upper compartment and at another end to said at least one spray arm assembly and an external air inlet line connected at one end to said upper compartment and at another end to a source of clean, filtered air;
   b) creating an airflow from said upper compartment to said lower compartment through said gap such that a curtain of air is formed along said side walls of said chamber;
   c) creating an airflow from said upper compartment to said lower compartment through said vent conduit and through said at least one spray arm assembly;
   d) creating an air flow from said lower compartment to said upper compartment through said opening;
   e) creating an airflow from said source of clean, filtered air to said upper compartment wherein said clean, filtered air mixes with air from said lower compartment to form a mixture of air;
   f) heating said mixture of air in said upper compartment to a temperature sufficient to vaporize fluid in said chamber before said mixture of air is forced through said gap and into said lower compartment; and
   g) venting a portion of said air in said lower compartment.

2. A method as defined in claim 1, wherein said method further includes a step of:
   providing a checkvalve within said vent conduit for preventing airflow through said vent conduit in a predetermined direction.

3. A method as defined in claim 1, wherein said washer further comprises:
   a valve assembly for varying the amount of clean, filtered air conveyed from said source of clean, filtered air to said upper compartment.

4. A method of drying articles within a washer, comprising the steps of:
   a) providing a washer having side walls that define a washing chamber, and providing a partition separating said chamber into an upper compartment and a lower compartment, said partition having an outer peripheral edge generally conforming to a shape defined by said side walls and being dimensioned to form a gap between said edge of said partition and said side walls of said chamber, said partition further including an opening centrally located in said partition, said upper compartment communicating with said lower compartment through said gap and through said opening, said washer including a heating means disposed in said upper compartment, at least one spray arm assembly disposed in said lower compartment for spraying fluid into said lower compartment and a blower assembly disposed in said upper compartment, said blower assembly having a first inlet fluidly communicating with said opening in said partition, a second inlet fluidly communicating with a source of clean filtered air and an air outlet fluidly communicating with said upper compartment;
   b) creating an airflow from said upper compartment to said lower compartment by forcing air from said air outlet of said blower assembly into said upper compartment and through said gap such that a curtain of air is formed along said side walls of said chamber;
   c) creating an air flow from said lower compartment to said upper compartment through said opening by drawing air from said lower compartment to said first inlet of said blower assembly wherein steps b) and c), in combination, create an airflow pattern wherein a portion of said curtain of air is drawn in a first direction across articles in said lower compartment and a portion of said curtain of air continues along said side walls and is redirected in a second direction across said articles in said lower compartment;
   d) heating said air in said upper compartment to a temperature sufficient to vaporize fluid in said chamber by said heating means disposed in said upper compartment;
   e) venting a portion of said air in said lower compartment out through an air vent tube; and
   f) introducing clean filtered air into said upper compartment by drawing air from said source of clean filtered air to said second inlet of said blower assembly wherein less than about 10% of said air flow from said upper compartment to said lower compartment is said clean, filtered air.

5. A method as defined in claim 1, wherein said first direction is perpendicular to said second direction.

6. A method as defined in claim 1, wherein another portion of said curtain of air is directed into corners of said chamber for drying said articles disposed near said corners of said chamber.

* * * * *